US010968283B2

(12) United States Patent
Andrews et al.

(10) Patent No.: US 10,968,283 B2
(45) Date of Patent: Apr. 6, 2021

(54) METHOD FOR PRODUCING FUNCTIONALIZED NANOCRYSTALLINE CELLULOSE AND FUNCTIONALIZED NANOCRYSTALLINE CELLULOSE THEREBY PRODUCED

(71) Applicant: Anomera Inc., Montréal (CA)

(72) Inventors: Mark P. Andrews, Westmount (CA); Timothy Morse, Montréal (CA)

(73) Assignee: Anomera Inc., Montreal (CA)

( * ) Notice: Subject to any disclaimer, the term of this patent is extended or adjusted under 35 U.S.C. 154(b) by 0 days.

(21) Appl. No.: 15/329,820

(22) PCT Filed: Jul. 27, 2015

(86) PCT No.: PCT/CA2015/050707
§ 371 (c)(1),
(2) Date: Jan. 27, 2017

(87) PCT Pub. No.: WO2016/015148
PCT Pub. Date: Feb. 4, 2016

(65) Prior Publication Data
US 2017/0260298 A1    Sep. 14, 2017

Related U.S. Application Data

(60) Provisional application No. 62/029,761, filed on Jul. 28, 2014.

(51) Int. Cl.
| *C08B 15/04* | (2006.01) |
| *A61K 8/73* | (2006.01) |
| *A61K 8/02* | (2006.01) |
| *A61Q 1/02* | (2006.01) |
| *A23L 29/262* | (2016.01) |
| *A61Q 1/06* | (2006.01) |
| *A61Q 1/12* | (2006.01) |
| *A61Q 3/02* | (2006.01) |
| *B01J 19/12* | (2006.01) |
| *C08J 5/18* | (2006.01) |
| *G01N 33/15* | (2006.01) |

(52) U.S. Cl.
CPC ............ *C08B 15/04* (2013.01); *A23L 29/262* (2016.08); *A61K 8/0241* (2013.01); *A61K 8/731* (2013.01); *A61Q 1/02* (2013.01); *A61Q 1/06* (2013.01); *A61Q 1/12* (2013.01); *A61Q 3/02* (2013.01); *B01J 19/123* (2013.01); *C08J 5/18* (2013.01); *G01N 33/15* (2013.01); *A23V 2002/00* (2013.01); *A61K 2800/10* (2013.01); *A61K 2800/413* (2013.01); *A61K 2800/436* (2013.01); *A61K 2800/654* (2013.01); *B01J 2219/0877* (2013.01); *B01J 2219/1203* (2013.01); *C08J 2301/08* (2013.01)

(58) Field of Classification Search
CPC ..................................................... C08B 15/04
USPC ......................................................... 536/77
See application file for complete search history.

(56) References Cited

U.S. PATENT DOCUMENTS

| 2,886,416 | A | * | 5/1959 | Cox ...................... C01B 15/023 423/589 |
| 5,769,934 | A | | 6/1998 | Ha et al. |
| 6,193,843 | B1 | | 2/2001 | Tsai et al. |
| 6,238,521 | B1 | | 5/2001 | Shing et al. |
| 6,544,548 | B1 | * | 4/2003 | Siller-Jackson ... A61K 47/6953 424/449 |
| 8,507,666 | B2 | | 8/2013 | Skuratowicz |
| 8,541,352 | B2 | | 9/2013 | Randall et al. |
| 9,139,662 | B2 | | 9/2015 | Tsuji et al. |
| 2008/0108772 | A1 | | 5/2008 | Oksman et al. |
| 2012/0009661 | A1 | | 1/2012 | Miyawaki et al. |
| 2013/0338250 | A1 | | 12/2013 | Umemoto et al. |
| 2014/0238626 | A1 | | 8/2014 | Tsuji et al. |
| 2014/0350188 | A1 | * | 11/2014 | Hamad ................. C08F 251/02 525/190 |
| 2015/0027648 | A1 | * | 1/2015 | Tsuji ...................... C08B 15/04 162/24 |
| 2015/0267070 | A1 | | 9/2015 | Tsuji et al. |
| 2016/0002457 | A1 | * | 1/2016 | Hamad ..................... C08F 2/44 522/72 |

FOREIGN PATENT DOCUMENTS

| CA | 2849750 | A1 |   | 4/2013 |          |
| CN | 102675475 | A |   | 9/2012 |          |
| EP | 0406837 | A2 |   | 1/1991 |          |
| GB | 417881 | A |   | 10/1934 |          |
| GB | 733364 | A | * | 7/1955 | ............... D21C 3/24 |

(Continued)

OTHER PUBLICATIONS

Babadagil et al. (2005) "Oil recovery performances of surfactant solutions by capillary imbibition," J. Colloid Interface Sci. 282:162-175.
Bai et al. (2009) "A technique for production of nanocrystalline cellulose with a narrow size distribution," Cellulose. 16:455-465.
Baranoski et al. (2004) "An Introduction to Light Interaction with Human Skin," Revista de Informatica Teorica e Aplicada (RITA). 1:33-60.
Beck-Candanedo et al. (2005) "Effect of Reaction Conditions on the Properties and Behavior of Wood Cellulose Nanocrystal Suspensions," Biomacromolecules. 6:1048-1054.
Dong et al. (1998) "Effect of microcrystallite preparation conditions on the formation of colloid crystals of cellulose," Cellulose. 5:19-32.

(Continued)

*Primary Examiner* — Shaojia A Jiang
*Assistant Examiner* — Everett White
(74) *Attorney, Agent, or Firm* — Lathrop GPM LLP; Brian C. Trinque, Esq.

(57) ABSTRACT

A method for producing functionalized nanocrystalline cellulose, the method comprising the steps of providing cellulose, mixing said cellulose with a peroxide, thereby producing a reaction mixture, and heating the reaction mixture, and/or exposing the reaction mixture to UV radiation is provided. Functionalized nanocrystalline cellulose produced by this method is also provided.

19 Claims, 10 Drawing Sheets

(56) References Cited

FOREIGN PATENT DOCUMENTS

| JP | 2012-076231 A | 4/2012 |
|---|---|---|
| WO | 1994/005851 A1 | 3/1994 |
| WO | 2000/015720 A1 | 3/2000 |
| WO | WO2004/011501 A1 | 2/2004 |
| WO | 2004072104 A2 | 8/2004 |
| WO | WO2006/015847 A1 | 2/2006 |
| WO | 2010/116826 A1 | 10/2010 |
| WO | 2011/040547 A1 | 4/2011 |
| WO | 2011/072365 A1 | 6/2011 |
| WO | WO2012/119229 A1 | 9/2013 |

OTHER PUBLICATIONS

Dufresne (2010) "Processing of Polymer Nanocomposites Reinforced with Polysaccharide Nanocrystals," Molecules. 15:4111-4128.
Elazzouzi-Hafraoui et al. (2008) "The shape and size distribution of crystalline nanoparticles prepared by acid hydrolysis of native cellulose," Biomacromolecules. 9:57-65.
Filpponen et al. (2010) "Regular linking of cellulose nanocrystals via click chemistry: synthesis and formation of cellulose nanoplatelet gels," Biomacromolecules. 11:1060-1066.
Habibi et al. (2010) "Cellulose nanocrystals: chemistry, self-assembly, and applications," Chemical Reviews. 110:3479-3500.
Hasani et al. (2008) "Cationic surface functionalization of cellulose nanocrystals," Soft Matter. 4:2238-2244.
Heath et al. (2010) "Cellulose nanowhisker aerogels," Green Chemistry. 12:1448-1453.
Holt et al. (2010) "Novel anisotropic materials from functionalised colloidal cellulose and cellulose derivatives," J. Mater. Chem. 20:10058-10070.
Iwamoto et al. (2009) "Elastic Modulus of Single Cellulose Microfibrils from Tunicate Measured by Atomic Force Microscopy," Biomacromolecules. 10:2571-2576.
Jiang et al. (2010) "Acid-Catalyzed and Solvolytic Desulfation of $H_2SO_4$-Hydrolyzed Cellulose Nanocrystals," Langmuir. 26:17919-17925.

Montanari et al. (2005) "Topochemistry of Carboxylated Cellulose Nanocrystals Resulting from TEMPO-Mediated Oxidation," Macromolecules. 38:1665-1671.
Nickerson et al. (1947) "Cellulose Intercrystalline Structure," Industrial & Engineering Chemistry. 39:1507-1512.
Nishikata et al. (1997) "A Natural-Looking Makeup," Cosmetics and Toiletries. 112:39-55.
Nishino et al. (2004) "All-Cellulose Composite," Macromolecules. 37:7683-7687.
Peng et al. (2011) "Chemistry and applications of nanocrystalline cellulose and its derivatives: a nanotechnology perspective," The Canadian Journal of Chemical Engineering. 9999:1-16.
Revol et al. (1992) "Helicoidal self-ordering of cellulose microfibrils in aqueous suspension," Int. J. Biol, Macromol. 14(3):170-172.
Sadeghifar et al. (2011) "Production of cellulose nanocrystals using hydrobromic acid and click reactions on their surface," Journal of Materials Science. 46:7344-7355.
Suchy et al. (2002) "Catalysis and activation of oxygen and peroxide delignification of chemical pulps: A review," TAPPI Journal. 1(2):1-18.
Zuluaga et al. (2007) "Cellulose microfibrils from banana farming residues: isolation and characterization," Cellulose. 14:585-592.
International Search Report with Written Opinion corresponding to International Patent Application No. PCT/CA2015/050707, dated Sep. 3, 2015.
Zhang, Yu Ping et al. (2013) "Structured Color Humidity Indicator From Reversible Pitch Tuning in Self-Assembled Nanocrystalline Cellulose Films," Sensors and Activators, vol. 176, pp. 692-697.
Fukuzumi et al. "Selective Permeation of Hydrogen Gas Using Cellulose Nanofibril Film." Biomacromolecules, Apr. 17, 2013 (Apr. 17, 2013), 5 pp.
Supplementary Partial European Search Report for EP 15826572 dated Jan. 4, 2018, 12 pp.
Leung et al., (2011) "Characteristics and Properties of Carboxylated Cellulose Nanocrystals Prepared from a Novel One-Step Procedure," SMALL, 7(3):302-305.
Lam et al. (2013) "Green Strategy Guided by Raman Spectroscopy for the Synthesis of Ammonium Carboxylated Nanocrystalline Cellulose and the recovery of Byproducts," ACS Sustainable Chem. Eng., 1:278-283.

* cited by examiner

A

B

A

B

METHOD FOR PRODUCING FUNCTIONALIZED NANOCRYSTALLINE CELLULOSE AND FUNCTIONALIZED NANOCRYSTALLINE CELLULOSE THEREBY PRODUCED

CROSS-REFERENCE TO RELATED APPLICATIONS

This application is a National Entry Application of PCT application no. PCT/CA2015/050707, filed on Jul. 27, 2015 and published in English under PCT Article 21(2), which itself claims benefit, under 35 U.S.C. § 119(e), of U.S. provisional application Ser. No. 62/029,761, filed on Jul. 28, 2014. All documents above are incorporated herein in their entirety by reference.

FIELD OF THE INVENTION

The present invention relates to a method for producing functionalized nanocrystalline cellulose and to the functionalized nanocrystalline cellulose produced by this method. More specifically, the present invention is concerned with a method for producing functionalized nanocrystalline cellulose from raw biomass.

BACKGROUND OF THE INVENTION

Cellulose is a hydrophilic semi-crystalline organic polymer, a polysaccharide that is produced naturally in the biosphere. It is the structural material of the cell wall of plants, many algae, and fungus-like micro-organisms called oomycetes. Industrially, cellulose is derived mainly from wood pulp and cotton. Cellulose is naturally organized into long linear chains of linked poly($\beta$-1,4-glucopyranose) units. These chains assemble by strong intra- and inter-molecular hydrogen bonds into highly crystalline 1.5-3.5 nm wide nano-fibrils. Regions of disordered (amorphous) cellulose can exist between these crystalline domains. The nano-fibrils assemble into larger micro-fibrils. Extensive hydrogen bonding among the cellulose polymer chains makes cellulose extremely resistant to dissolution in water.

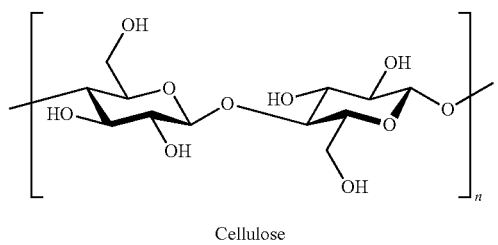

Cellulose

Cellulose can be converted to microcrystalline cellulose, a powdered form that is used as an inert filler in drug tablets, and as a thickener and stabilizer in cosmetics and processed foods.

Cellulose nano-fibrillar domains are generally referred to as nanocellulose. Under certain conditions, these domains can be separated from each other by strong chemical acids, intense mechanical forces or by specific enzymes. By breaking chemical bonds in the amorphous regions, cellulose can be converted to cellulose nanocrystals, also called cellulose whiskers, nanocrystalline cellulose (NCC) or crystalline nanocellulose (CNC).

NCC is typically made by hydrolysis of the components of wood pulp, where the amorphous regions of cellulose in the pulp are broken down to liberate the nanocrystals. In particular, NCC is prepared by acid hydrolysis using concentrated sulfuric acid. The sulfuric acid procedure esterifies the surface of NCC with sulfate (—O—S$_3$-) groups. The sulfuric acid method under fixed conditions can yield crystallites of fairly uniform size when the cellulose is derived from a single source. Hydrochloric, hydrobromic and mixed acetic-nitric acids are also capable of hydrolysing cellulose to yield NCC without adding ester functionalities to the surface. Inorganic persulfates, like ammonium persulfate, when used at elevated temperatures, can produce nanocrystalline cellulose from vegetative biomass in one step. The NCC so produced is modified to varying amounts with a carboxylic acid (—COOH) group (apparently located at the CU position of the glucopyranose ring).

The sulfuric acid hydrolysis method to make NCC has been scaled to an industrial process; but this method has several disadvantages: it is costly because it requires large capital investment in equipment and operating expense due to the use of corrosive sulfuric acid; it requires heightened levels of safety for acid materials handling, waste disposal and treatment; It requires pre-treatment of the cellulose source with alkali and/or bleaching chemicals to remove non-cellulosic content in the form of lignin, pectin and hemicellulose. Moreover, the Industrial sulfuric acid method imparts sulfate ester groups to the NCC; but these are not easily amenable to chemical modification.

Chemical modification of the surface of the NCC is highly desirable. It can indeed make the NCC more amenable to suspension in organic solvents, or make it more chemically active for combination with drug compounds, dye molecules, monomer molecules to make polymer composites, flexible plastic films, and other compositions of matter where the properties of the material might be altered by addition of the NCC. To date, most procedures to modify NCC for these purposes rely on the use of emulsifiers and heterogeneous chemical reactions at the glucopyranose hydroxyl moieties. In some cases, the C6 position of the glucopyranose ring is targeted because it shows selective reactivity in respect of chemical functionalization, without breaking the chemical bonds (degrading) the hexose ring structure.

A chemically versatile functional group for chemical modification is the carboxylic acid group. Conventionally, the carboxylic acid group is introduced by a process called TEMPO oxidation or by periodate oxidation. Periodate oxidation breaks the hexose ring structure. These processes to introduce carboxylic acid in the C6 position are not industrially scalable due to cost and complexity of chemical processing.

Turning now to another subject, oxidizing agents, such as hydrogen peroxide, are commonly used to bleach wood pulp. Bleaching is the chemical process of altering the color of pulp towards white. Hydrogen peroxide can be degraded into hydroxyl radicals by the absorption of ultraviolet light. In turn, hydroxyl radicals will oxidize some organic compounds. In this way, the action of hydrogen peroxide as a bleaching agent can be altered by the application of ultraviolet light. Peroxymonosulfuric acid (Caro's acid) is a bleaching oxidizing agent prepared from the reaction of hydrogen peroxide with sulfuric acid. Dimethyldioxirane generated from the reaction of acetone with Caro's acid behaves as a bleaching agent. Persulfates like ammonium persulfate can also be used, in combination with metal ion catalysts, to bleach pulp. Despite interest in these bleaching systems, their incompatibility with existing energy recovery systems, concerns over safety, and impact on the environment prevents widespread industrial use.

Turning to yet another subject, lignin is a material that is removed from pulp before bleached (white) paper can be manufactured. Lignin is an integral part of the secondary cell walls of plants. It is a complex polymer of aromatic alcohols. Hydrogen peroxide alone shows limited reactivity toward residual lignin. Hydrogen peroxide in combination with dioxygen has been used for delignification since the 1980s. Usually, hydrogen peroxide is activated with alkali, diethylenetriamine pentaacetic acid (DTPA) with acid pretreatment, or in combination with cyanide, polyoxometallates or metal cations to enhance its interaction with oxygen. Pretreating pulp with peroxyformic acid prior to a peroxide stage seems to increase delignification. Peracetic acid has also been used for delignification. It is prepared by mixing acetic acid with hydrogen peroxide in the presence of sulfuric acid catalyst.

On yet another subject, it is known that certain cationic poly electrolytes can be combined with cellulose surfaces to confer a positive charge on the surface of cellulose. For example U.S. Pat. No. 6,238,521 teaches that polydiallyldimethylammonium chloride (PDDA, also called polyquaternium-6) can be used as a wet-end additive in the papermaking process. Also, Randall et al. teach in U.S. Pat. No. 8,541,352 that cationic polymers can be used to impart desirable surface properties to materials like hair and fabrics.

On another subject, there is a need for a cosmetic foundation that gives the user a natural look that provides a natural sheen that resembles or duplicates the look of healthy skin, i.e. a healthy glow and a natural color. Nevertheless, it is difficult to have a foundation cosmetic that simultaneously covers skin flaws, creates even skin tones and yields the healthy and vibrant glow of clean and clear skin. These desirable properties are difficult to satisfy simultaneously. Much research has been devoted to understanding the optical properties of skin. These studies have focused on optical properties of skin that include absorption, scattering, transmittance, reflection and the spatial energy distribution of light (Nishikata et al., Cosmetics and Toiletries, 112, 39-55, 1997; G. Baranoski and A. Krishnaswamy, An Introduction to Light Interaction with Human Skin, Revista de Informatica Teorica e Aplicada (RITA) XI, no. 1, 2004, 33-60). Sometimes spherical particles are used to impart enhanced feel. WO 00115720 discloses a pigment mixture that incorporates spherical $SiO_2$ particles exhibiting high light scattering. Some of the particles are coated with $TiO_2$ and some are coated with $Fe_2O_3$. From the prior art, these fillers are known to have relatively good skin feel. They have the disadvantage however of a white unnatural appearance on the skin. This is due in part to the fact that the presence of surface particles on the spheres increases light scattering or attenuates (absorbs) light. It is also a disadvantage that these spherical particles are made from glass. Thus it is desired that the spherical particle act as a diffuser, reflector and refractor in order to provide the look of skin having a uniform surface topography (reduced look of wrinkles and lines) whilst providing a natural healthy glow, the illusion of sheerness and translucency that imitates the sheen of natural skin. It is also desired to have a spherical particle that exhibits these properties and that is also derived from natural or renewable resources, preferably from cellulosics or cellulose biomass.

On a last subject, it is noted that, conventionally, a positive surface charge can be conferred on sulfated nanocrystalline cellulose by covalent attachment of an alkyl ammonium salt. For example, Gray et al. (M. Hasani, E. Cranston, G. Westman and D. Gray, Soft Matter, 2008, 4, 2238-2244) describe a method to create a positive surface charge on nanocrystalline cellulose by covalent attachment of epoxypropyltrimethylammonium chloride. This reaction requires basic conditions (elevated pH) that change the crystal structure of the nanocrystalline cellulose.

SUMMARY OF THE INVENTION

In accordance with the present invention, there is provided:
1. A method for producing functionalized nanocrystalline cellulose, the method comprising the steps of:
   (a) providing cellulose,
   (b) mixing said cellulose with a peroxide, thereby producing a reaction mixture, and
   (c) heating the reaction mixture, and/or
   (c') exposing the reaction mixture to UV radiation,
   steps (c) and/or (c') thereby producing carboxylated nanocrystalline cellulose as said functionalized nanocrystalline cellulose.
2. The method of item 1, wherein the peroxide is hydrogen peroxide, an organic peroxide, or a mixture thereof.
3. The method of item 2, wherein the peroxide is aqueous hydrogen peroxide.
4. The method of any one of items 1 to 3, wherein the peroxide is present in the reaction mixture at a concentration between about 10 to about 40%.
5. The method of item 4, wherein the peroxide is present in the reaction mixture at a concentration between about 10 and about 30%.
6. The method of item 5, wherein the peroxide is present in the reaction mixture at a concentration between about 20 and about 30%.
7. The method of any one of items 1 to 6, wherein the reaction mixture is heated in step (c) at a temperature up to and including reflux.
8. The method of item 7, wherein the temperature in step (c) is between about 50° C. and reflux.
9. The method of item 8, wherein the temperature in step (c) is between about 100° C. to reflux.
10. The method of item 9, wherein the temperature in step (c) is reflux.
11. The method of any one of items 1 to 10, wherein the reaction mixture is exposed in step (c') to UV radiation in the range from about 200 to about 350 nm.
12. The method of item 11, wherein the reaction mixture is exposed in step (c') to UV radiation in the range from about 260 to about 280 nm.
13. The method of any one of items 1 to 12, wherein the reaction mixture is at a temperature in the range of 15-30° C. during step (c).
14. The method of item 13, wherein the reaction mixture is at a temperature in the range of about 20 to about 25° C. during step (c').
15. The method of any one of items 1 to 14, wherein step (c) is carried out and step (c') is not carried out.
16. The method of any one of items 1 to 14, wherein step (c') is carried out and step (c) is not carried out.
17. The method of any one of items 1 to 14, wherein steps (c) and (c') are carried out consecutively.
18. The method of any one of items 1 to 12, wherein at least part of steps (c) and (c') are carried out concurrently.
19. The method of any one of items 1 to 12, wherein all of steps (c) and (c') are carried out concurrently.

20. The method of any one of items 1 to 19, further comprising the step (d) of salifying the functionalized nanocrystalline cellulose, thereby producing a nanocrystalline cellulose carboxylate salt as a further functionalized nanocrystalline cellulose.
21. The method of item 20, further comprising the step (e) of positively charging the surface of the nanocrystalline carboxylate salt cellulose by:
   (e') providing an aqueous suspension of the nanocrystalline cellulose carboxylate salt,
   (e") mixing said suspension with a water soluble cationic polyelectrolyte to form a reaction mixture, and
   (e''') sonicating the reaction mixture, thereby producing an aqueous suspension of a nanocrystalline cellulose carboxylate salt having a positive surface charge as a further functionalized nanocrystalline cellulose.
22. The method of any one of items 1 to 21, further comprising step (f) of isolating the functionalized nanocrystalline cellulose.
23. The method of item 22, wherein said isolation is carried out by centrifugation.
24. The method of item 22, wherein said Isolation is carried out by diafiltration.
25. The method of any one of items 1 to 24, further comprising step (g) of spray-drying the functionalized nanocrystalline cellulose.
26. The method of any one of items 1 to 25, further comprising step (h) of recycling unreacted peroxide.
27. Functionalized nanocrystalline cellulose produced by a method according to any one of items 1 to 26.
28. The functionalized nanocrystalline cellulose of item 27, being carboxylated nanocrystalline cellulose.
29. The functionalized nanocrystalline cellulose of item 27, being a nanocrystalline cellulose carboxylate salt.
30. The functionalized nanocrystalline cellulose of item 30, being nanocrystalline cellulose sodium carboxylate.
31. The functionalized nanocrystalline cellulose of any one of items 27 to 30 having a negative surface charge.
32. The functionalized nanocrystalline cellulose of any one of items 27 to 30 having a positive surface charge.
33. The functionalized nanocrystalline cellulose of any one of items 27 to 32, comprising cellulose nanocrystals that are between about 2 nm to about 20 nm in width and between about 80 nm and about 250 nm in length.
34. The functionalized nanocrystalline cellulose of item 33, wherein the cellulose nanocrystals are between about 5 nm to about 10 nm in width and between about 100 nm and about 150 nm in length.
35. The functionalized nanocrystalline cellulose any one of items 27 to 34 being in dried powder form.
36. The functionalized nanocrystalline cellulose of item 35, being in the form of spherical particles.
37. The functionalized nanocrystalline cellulose of item 35 or 36, wherein the functionalized nanocrystalline cellulose has been spray-dried,
38. Use of the functionalized nanocrystalline cellulose of any one of items 27 to 34 as a humidity indicator.
39. Use of the functionalized nanocrystalline cellulose of item 29 or 30 as a humidity indicator.
40. A humidity indicator comprising the functionalized nanocrystalline cellulose of any one of items 27 to 33
41. A humidity indicator comprising the functionalized nanocrystalline cellulose of item 29 or 30.
42. Use of the functionalized nanocrystalline cellulose of any one of items 27 to 37 in the manufacture of a cosmetic preparation.
43. Use of the functionalized nanocrystalline cellulose of any one of items 35 to 37 in the manufacture of a cosmetic preparation.
44. The use of item 43, wherein the functionalized nanocrystalline cellulose is carboxylated nanocrystalline cellulose or a nanocrystalline cellulose carboxylate salt with a positive surface charge.
45. A cosmetic preparation comprising the functionalized nanocrystalline cellulose of any one of items 27 to 37.
46. A cosmetic preparation comprising the functionalized nanocrystalline cellulose of any one of items 35 to 37.
47. The cosmetic preparation of item 46, wherein the functionalized nanocrystalline cellulose is carboxylated nanocrystalline cellulose or a nanocrystalline cellulose carboxylate salt with a positive surface charge.
48. A method for positively charging the surface of a nanocrystalline cellulose, the method comprising the steps of:
   a. providing an aqueous suspension of the nanocrystalline cellulose,
   b. mixing said suspension with a water soluble cationic polyelectrolyte to form a reaction mixture, and
   c. sonicating the reaction mixture, thereby obtaining an aqueous suspension of the nanocrystalline cellulose with a positive surface charge.

DETAILED DESCRIPTION OF THE INVENTION

Figure 1:
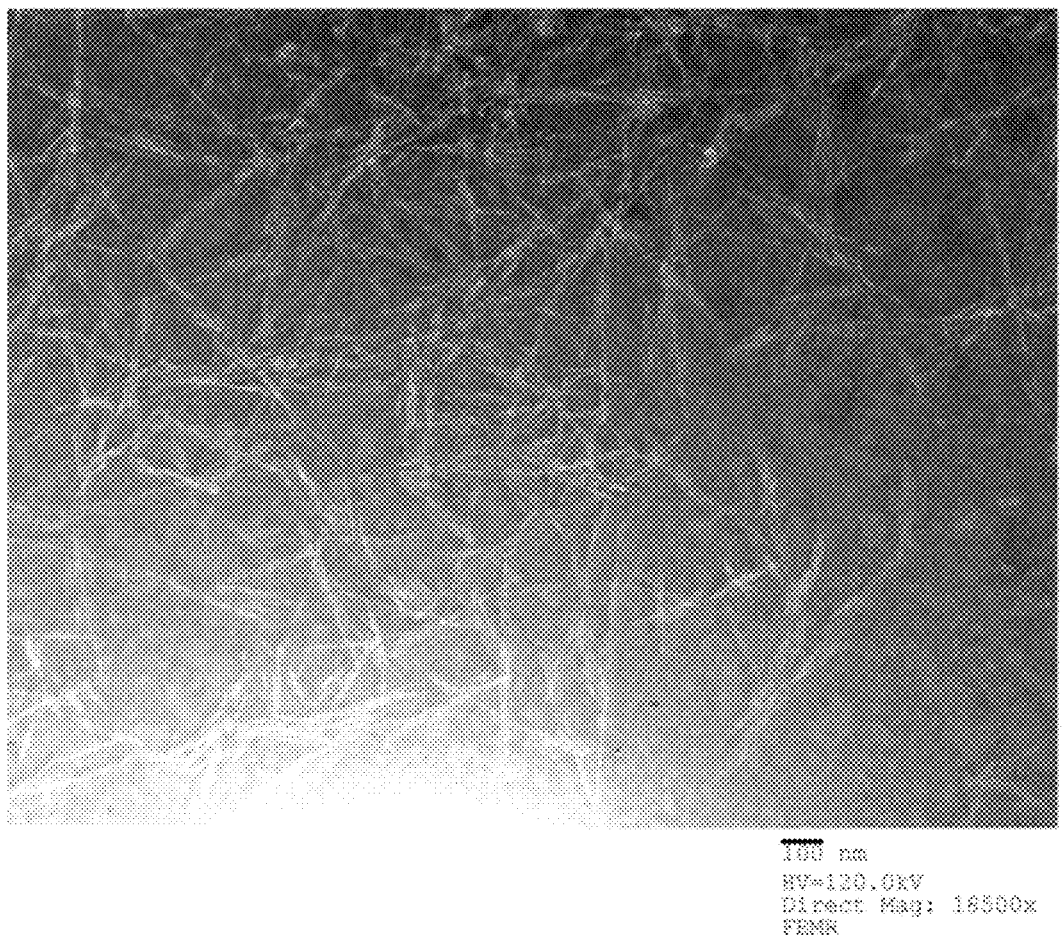
FIG. 1 is the transmission electron micrograph (TEM) of the carboxylated NCC produced in Example 1.

Turning now to the invention in more detail, there is provided a method for producing functionalized nanocrystalline cellulose and the functionalized nanocrystalline cellulose produced by that method Method for Producing Functionalized Nanocrystalline Cellulose In a first aspect of the invention, a method for producing functionalized nanocrystalline cellulose is provided. This method comprises the steps of:
(a) providing cellulose,
(b) mixing said cellulose with a peroxide, thereby producing a reaction mixture, and
(c) heating the reaction mixture, and/or
(c') exposing the reaction mixture to UV radiation.

This method takes advantage of the fact that, as surprisingly found by the present inventors, peroxides can be used to successfully produce nanocrystalline cellulose from cellulose.

The cellulose provided at step (a) can be of various sources. An appropriate source of biomass can be, for example, cellulose-based materials that have undergone extensive treatment to remove lignin (e.g. paper), wood pulp, microcrystalline cellulose, microfibrillated cellulose, and so on. Advantageously, the cellulose source can be raw vegetative biomass, which can be wood chips, sawdust, cardboard, hemp, the genus Linum (flax), straw from the stalks of cereal grains, and other sources. The cellulose source can also be in the form of a powder.

The peroxide can be hydrogen peroxide ($H_2O_2$), an organic peroxide, or a mixture thereof. The organic peroxide can be one of the so-called Class 5.2 organic peroxides (according to the IMO Classes for Dangerous Goods). These comprise peroxides with the linkage —O—O— and may be considered derivatives of hydrogen peroxide where one or more of the hydrogen atoms is replaced by an organic functional group. These include organic peroxides of formula ROCR', wherein R is alkyl, alkyloyl, alkyloxycarbonyl, aryl, aryloyl, or aryloxycarbonyl and R' is H, alkyl, alkyloyl, alkyloxycarbonyl, aryl, aryloyl, or aryloxycarbonyl; the alkyl, alkyloyl, alkyloxycarbonyl, aryl, aryloyl, or aryloxycarbonyl being unsubstituted or substituted. Non-limiting examples of alkyl include methyl, ethyl, propyl, butyl and t-butyl; non-limiting examples of alkyloyl include ethyloyl, propyloyl and butyloyl; non-limiting examples of alkyloxycarbonyls include carbonate esters such as ethyl carbonate, propylcarbonate, butyl carbonate; non-limiting examples of aryl include phenyl, benzyl, chlorobenzyl, naphthyl, thienyl, indolyl; non-limiting examples of aryloyl include phenyloyl and naphthyloyl; non-limiting examples of aryloxycarbonyls include carbonate esters such as phenyl carbonate and naphthyl carbonate.

Non-limiting examples of organic peroxides include:
dialkylperoxides of the formula $R_1$—O—O—$R_1$, wherein $R_1$ represents the same or different alkyl groups;
diarylperoxides of the formula $R_2$—O—O—$R_2$, wherein $R_2$ represents the same or different aryl groups, for example dibenzylperoxide;
hydroperoxides of the formula $R_3$—O—O—H, where $R_3$ is an alkyl or aryl group;
peroxycarboxylic acids of the formula $R_3$—C(=O)—O—O—H, where $R_3$ is an alkyl or aryl group;
di-acylperoxides of the formula $R_4$—C(=O)—O—O—C(=O)—$R_4$, where $R_4$ represents the same or different alkyl or aryl groups, for example dibenzoylperoxide;
peroxydicarbonates of the formula $R_4$—O—C(=O)—O—O—C(=O)—O—$R_4$, wherein $R_4$ is as defined above, for example, di-n-propylperoxydicarbonate;
peroxyesters of the formula $R_4$—O—O—C(=O)—$R_4$, wherein $R_4$ is as defined above; and
alkylperoxycarbonates of the formula $R_4$—O—O—C(=O)—O—$R_4$, wherein $R_4$ is as defined above.

In embodiments, the organic peroxide is dibenzoylperoxide, or a peroxycarboxylic acid. Preferably, the peroxide is or comprises $H_2O_2$.

Generally, the peroxide in the reaction mixture can be at a concentration in the range of 10 to 40%, preferably 20%. As will be well-known to the skilled person, care should be taken to avoid explosions when using peroxides, especially at higher concentrations.

The reaction mixture will generally also comprise a solvent, typically an aqueous solvent, generally water. Of note, this solvent can be the solvent in which the peroxide is commercially provided.

In embodiments, the peroxide is aqueous hydrogen peroxide. In these embodiments, the aqueous hydrogen peroxide in the reaction mixture can be at a concentration in the range of 10 to 40%, preferably 30%, in water.

When energy is provided into the system, via heating or UV radiation, the peroxide will hydrolyse the cellulose to provide nanocrystalline cellulose-bearing carboxylic (—COOH) groups.

At step (c), the reaction mixture is heated at a temperature above room temperature up to and including reflux. It should be noted that higher temperatures tend to speed up the reaction. In embodiments, this temperature is between about 50° C. and reflux (the latter depending on the mass of cellulosic material in the flask and the initial concentration of the hydrogen peroxide). Preferably, this temperature is between about 70° C. and reflux. More preferably, this temperature is reflux.

At step (c'), the reaction mixture is exposed to ultra-violet (UV) radiation. This UV radiation can be in the range of about 200 to about 350 nm, preferably in the range from about 260 to about 280 nm. Shorter wavelength radiation gives a higher probability of bond breaking. Larger doses (the product of intensity and time) will give a higher probability of bond breaking.

UV exposition can be conducted at a temperature around or slightly below or above room temperature, for example at a temperature in the range of 15-30° C., for example in the range of about 20 to about 25° C. However, UV exposition can also be conducted at higher temperatures. In other words, parts or the whole of steps (c) and (c') can be carried out concurrently. Of course, steps (c) and (e) can also be carried out consecutively (in any order). Alternatively, only one of step (c) and (c') can be carried out.

During steps (c) and (c'), it is preferable that the reaction mixture be stirred as this homogenizes the reaction mixture and thereby eases the reaction.

Steps (c) and (c') typically last between about 30 minutes and 12 about hours. They can last, for example, for about 8 hours. The length of steps (c) and (c') will depend on the desired yield, the source of cellulose used, the temperature of the reaction mixture, and the intensity of the UV radiation. For example, it may require up to 8 hours to produce NCC by heating peroxide in the absence of UV light. It may require 12 or more hours to convert biomass to NCC from peroxide when the mixture is irradiated with UV light alone at room temperature.

Advantageously, steps (c) and (c') are carried out in the absence of:
mineral acids (such as sulfuric acid hydrochloric acid, hydrobromic acid, peroxymonosulfuric acid, acetic-nitric acid mixture),
organic acids other than the above peroxycarboxylic acids (such as acetic acid, diethylenetriamine pentaacetic acid),
inorganic persulfates (such as ammonium persulfate), alkalis,
cyanide,
polyoxometallates, and/or
metal cations.

Carboxylated Nanocrystalline Cellulose

The functionalized nanocrystalline cellulose produced by the above method has surface carboxylic (—COOH) groups and hereinafter will also be referred to as carboxylated nanocrystalline cellulose or as the "acid form". Such functionalization can be advantageous as these groups are convenient handles for further chemical modification. Also, unless further modified, the carboxylated nanocrystalline cellulose produced by the above method is essentially free of surface sulfate groups, which are rather introduced by other methods for producing nanocrystalline cellulose.

Typically, the carboxylated nanocrystalline cellulose produced by the above method is comprised of cellulose nanocrystals having dimensions in width of 2 to 20 nm and in length, 80-250 nm, for example dimensions in width of 5 to 10 nm and in length, 150-200 nm.

Typically, the carboxylated nanocrystalline cellulose is obtained as a precipitate in water (which is used as a reaction solvent). It can then be further Isolated/purified, spray-dried, or modified. All these options will be described below.

In an aspect, the present invention provides carboxylated nanocrystalline cellulose produced by the above method and being as described above.

Optional Additional Step (d)—Salification

In embodiments, the method of the invention further comprises the step (d) of salifying the carboxylated nanocrystalline cellulose as produced above to produce a nanocrystalline cellulose carboxylate salt as a further functionalized nanocrystalline cellulose.

Such salt is preferably an alkali metal salt and the functionalized NCC produced is a nanocrystalline cellulose alkali metal carboxylate salt.

Salification can be achieved, for example, by reacting the carboxylic groups in the functionalized nanocrystalline cellulose with an appropriate base. For example, sodium hydroxide will transform at least part of the carboxylic (—COOH) groups of the carboxylated nanocrystalline cellulose into sodium carboxylate (—COO$^-$ $^+$Na) groups (hereinafter this specific NCC will be referred to as nanocrystalline cellulose sodium carboxylate salt).

Nanocrystalline Cellulose Carboxylate Salts

The nanocrystalline cellulose carboxylate salts, for example the alkali metal salts, such as the sodium salt, for example, are typically obtained in the form of suspensions in water (which is used as the reaction solvent).

These salts generally have a negative surface charge.

They are generally in the form cellulose nanocrystals having about the same dimensions as those discussed above.

These nanocrystalline cellulose carboxylate salts can further be isolated/purified, spray-dried, or modified. All these options will be described below.

In an aspect, the present invention provides nanocrystalline cellulose carboxylate salts produced by the above method and being as described above.

Optional Additional Step (e)—Positively Charging the Surface

In embodiments, the method of the invention further comprises the step (e) of positively charging the surface of the above nanocrystalline cellulose carboxylate salts. This can be achieved by:

(e') providing an aqueous suspension of the nanocrystalline cellulose carboxylate salt, (e") mixing said suspension with a water soluble cationic polyelectrolyte to form a reaction mixture, and (e''') sonicating the reaction mixture, thereby obtaining a suspension of a nanocrystalline cellulose carboxylate salt having a positive surface charge as a further functionalized nanocrystalline cellulose.

Regarding step (e'), it should be noted that, when applicable, the aqueous suspension provided can be that obtained from step (d). In other words, the product of step (d) can be directly used in step (e').

Examples of suitable cationic polyelectrolyte include, but are not restricted to, polyquaternium species that are well-known for example in the personal care products industry. Polyquaterniums are identified as polyquaternium-1, -2, -4, -5 to -20, -22, -24, -27 to -37, -39, -42, -44 to -47. A preferred polyquaternium is polydiallyldimethylammonium chloride (PDDA, also called polyquaternium-6). Other cationic polymers include poly(ethyleneimine), pol-L-lysine, poly(amidoamine)s and poly(amino-co-ester)s.

The advancement of the reaction can be followed by monitoring the zeta potential as shown in Example 7 below.

This method takes advantage of the strong electrostatic binding between the water soluble cationic polyelectrolyte and the anionic carboxylate surface groups.

This method is useful because for some applications, it may be desirable to change the surface potential so that they have a positive surface charge. Indeed, in some cases there may be benefit to having nanocrystalline cellulose bearing a positive potential.

This method is also useful because it results in an aqueous suspension in which the surface charge is reversed without diminishing the dispersibility of the nanocrystalline cellulose. Indeed, with respect to nanocrystalline cellulose, and in particular in respect to the carboxylate anion of nanocrystalline cellulose, there is a need to disperse the individual nanocrystallites. Indeed, dispersion at such a small scale is desirable because:

a. mechanical properties of composites (like polymer composites) are well-known to depend on the degree of dispersion;

b. the nanocrystals can be more effectively coated or modified when individual nanocrystallites are provided; and c. solid films comprising composites of individual nanocrystallites and other components like polymers can be produced in forms that are optically transparent and a transparent nanocomposite solid film state cannot be produced from aggregated nanocrystalline cellulose.

Nanocrystalline Cellulose Carboxylate Salts with a Positive Surface Charge

The above method produces aqueous suspensions of a nanocrystalline cellulose carboxylate salt with a positive surface charge. More specifically, the nanocrystalline cellulose carboxylate salt with a positive surface charge is in the form of individual cellulose nanocrystallites where the surface of the nanocrystallites has been rendered positive. Since the starting nanocrystalline cellulose carboxylate salt had a negative surface charge, this means that the surface charge has been reversed.

The nanocrystalline cellulose carboxylate salt with a positive surface charge can further be isolated/purified or spray-dried. Both these options will be described below.

In an aspect, the present invention provides nanocrystalline cellulose carboxylate salt with a positive surface charge produced by the above method and being as described above.

The Method for Positively Charging the Surface is Not Limited

The above method to positively charge the surface of functionalized nanocrystalline cellulose is not restricted to the nanocrystalline cellulose carboxylate salts described in the previous sections. Other types of nanocrystalline cellulose, especially those bearing a negative charge, can be converted to a positive charge. One example of other nanocrystalline cellulose includes sulfated nanocrystalline cellulose, and also carboxylated nanocrystalline cellulose prepared by other methods such as TEMPO oxidation.

In such cases, the method for positively charging the surface of a nanocrystalline cellulose comprises the steps of:
 a. providing an aqueous suspension of the nanocrystalline cellulose,
 b. mixing said suspension with a water soluble cationic polyelectrolyte to form a reaction mixture, and
 c. sonicating the reaction mixture, thereby obtaining an aqueous suspension of a nanocrystalline cellulose with a positive surface charge.

Optional Additional Step (f)—Isolation

Typically, as seen above, the functionalized nanocrystalline cellulose is obtained as a precipitate or in the case of carboxylate salts with either positive or negative surface charge, as suspensions of solid particles in a liquid.

In all cases, in embodiments, the method further comprises step (f) isolating the functionalized nanocrystalline cellulose. This isolation can be carded out, for example, by centrifugation or diafiltration.

This step has the further advantage of purifying the functionalized nanocrystalline cellulose.

Step (f) can be performed after one or more of step (c), (c'), (d), and (e) and/or in between any of these steps. Indeed, it may be desirable to perform step (f) to purify a final product and/or to purify a product between using it in one of the optional steps described herein. Therefore, step (f) can be performed several times at different stages of the method of the invention.

Optional Additional Step (g)—Spray-Drying

In other embodiments, the method further comprises step (g) of spray-drying the functionalized nanocrystalline cellulose.

Step (g) can be performed after step (c), (c'), (d), (e) or (f) or in between any of these steps. Preferably, it is performed after one of these steps, not in between these steps. Indeed, as discussed below, spray-drying produces solid particles with desirable characteristics. Therefore, it is preferable to perform step (g) last so as to obtain a final product that will embody these desirable characteristics.

As stated above, the functionalized nanocrystalline cellulose prepared by the above method is typically obtained as an aqueous suspension (for carboxylate salts with either positive or negative surface change) or as a precipitate in water (for the add form). It is desirable to have a method to obtain dried powder forms of these products.

Powdered, dried forms can be obtained by a process called spray drying, In this process, a feed pump is used to impel a fluid suspension of the nanocrystalline cellulose towards a drying chamber. Prior to reaching the chamber, the fluid is briefly mixed with hot air, which has been heated to an inlet temperature ($T_{in}$), before being sprayed through a nozzle specifically designed to create small droplets. Droplet size is controlled by the inlet pressure. The high temperature within the drying chamber, combined with high pressure expulsion of an aerosol of micro-droplets, causes near-instantaneous evaporation of the liquid, depositing a very fine dry powder. A fan, or other source of moderate vacuum, is used to draw the hot water vapour and fine particles from the drying chamber to a region called the cyclone. In the cyclone, nanocrystalline cellulose particles are separated from gas. The water vapour is exhausted from the system, while the particles are collected.

Typically, the carboxylated nanocrystalline cellulose powder thus obtained is white in color. In contrast, nanocrystalline cellulose produced according to the teachings of WO2011/072365 is brown.

An advantage of spray drying nanocrystalline cellulose is that the product is concentrated as a powder. This makes it easier to package, ship, store and use the material.

Another advantage of spray drying, in the case of carboxylated nanocrystalline cellulose or the nanocrystalline cellulose carboxylated salts (with either a positive or a negative surface charge), is that the nanocrystallites can be aggregated into spherical particles whose diameter can be controlled by process variables like pressure and temperature in the spray drying unit. Spherical particles are desired in certain commercial applications like the creation of excipients for the pharmaceutical industry or the production of some cosmetic products that rely on enhanced "feel" and optical properties that improve the appearance of the color of skin and the appearance of the reduction of wrinkles.

Functionalized Nanocrystalline Cellulose in Dried Powder Form

The above spray drying produces functional nanocrystalline cellulose (the acid from and carboxylate salts with either positive or negative surface charge) in dried powder form. More specifically, the functional nanocrystalline cellulose is in the form of spherical particles. The diameter of these particles and their diameter distribution can be controlled.

In an aspect, the present invention provides functionalized nanocrystalline cellulose in dried powder form produced by the above method and being as described above.

Optional Additional Step (h)—Recycling of Unreacted Peroxide

In embodiments, the method further comprises step (h) of recycling unreacted peroxide. This unreacted peroxide is the peroxide that has not been consumed in the preparation of the functionalized nanocrystalline cellulose. For example, this peroxide can be reused in the above-described method.

Step (h) can be performed independently of the presence or absence of any and all the optional steps discussed above. It can be performed as soon as the peroxide has played its role in the reaction to form the functionalized nanocrystalline cellulose from the starting cellulose.

Advantages of the Method of the Invention

As discussed above, the method of the invention advantageously produces nanocrystalline cellulose functionalized with surface carboxylic (—COOH) groups, which can be modified.

Further, in embodiments, the method of the invention can present one or more of the following advantages.
 It allows producing carboxylated NCC in one-step. (Further purification may be needed.)
 It has reduced negative impact on the environment.
 It is cost effective.
 It is free of chlorine and phosphates.
 It does not use inorganic compounds and ions. Indeed, unlike inorganic peroxides (ammonium persulfate, for example) that produce sulfate and other inorganic ions after reaction, the present method produces only water as the primary decomposition product of the breakdown of hydrogen peroxide. If therefore does not require the treatment of contaminants like inorganic ions.

It does not require concentrated acids. Thus, it does not require treatment of contaminants or waste management associated with the use of acids. There are also fewer safety concerns involved with the use of the present method.

It has reduced costs for energy recovery.

It does not require inorganic catalysts to oxidize the biomass.

It does not require pre-processing of the cellulose source. Indeed, in contrast to prior art acid hydrolysis processes, it does not require purification (by steam-exploding, or by bleaching, for example) of the biomass cellulosic material. The use of raw biomass may reduce the cost of NCC production.

Potential Applications

Humidity Indicators-Iridescence

The above nanocrystalline cellulose carboxylate salts can exhibit iridescence—see Example 6 below. This suggests that they could find applications—for example in the form of dry and wet films—as humidity indicators e.g. for food and pharmaceuticals.

Therefore, in an aspect of the invention, there Is provided a humidity indicator comprising the above functionalized nanocrystalline cellulose, and more specifically the carboxylate salts with the negative surface charge.

The present invention is thus also concerned with the use of these functionalized nanocrystalline cellulose, for example in the form of dry films or wet films, as humidity indicators.

Cosmetics

In another aspect of the present invention, there Is provided a cosmetic preparation comprising the above functional nanocrystalline cellulose. The present invention is thus also concerned with the use of these functionalized nanocrystalline cellulose in the manufacture of a cosmetic preparation.

Indeed, desirable properties and effects may be achieved by a composition comprising the functionalized nanocrystalline cellulose of the invention, and more preferably that in the form of spherical particles obtained by spray drying. These may act as diffusers, reflectors and refractors. Preferably the spherical particles, either of the acid form or the carboxylate salts with a positive surface charge, should be dispersible in water and ingredients used to formulate cosmetic preparations. Such preparation may be for example a foundation, a gloss, a nail polish, and a lipstick.

Definitions

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure with various substituents and various radicals enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as commonly understood by one of ordinary skill in the art to which this invention belongs.

For certainty, it should be noted that:
alkyloyl is alkyl-C(=O)—,
aryloyl is aryl-C(=O)—,
alkyloxycarbonyl is alkyl-O—C(=O)—, and
aryloxycarbonyl is aryl-O—C(=O)—.

Herein, the terms "alkyl" has its ordinary meaning in the art. It is to be noted that, unless otherwise specified, the hydrocarbon chain of the alkyl groups can be linear or branched. Further, unless otherwise specified, these groups can contain between 1 and 18 carbon atoms, more specifically between 1 and 12 carbon atoms, between 1 and 6 carbon atoms, between 1 and 3 carbon atoms, or contain 1 or 2 carbon atoms.

Herein, the terms "aryl" has its ordinary meaning in the art. It is to be noted that, unless otherwise specified, the aryl groups can contain between 5 and 30 atoms, including carbon and heteroatoms, preferably without heteroatoms, more specifically between 5 and 10 atoms, or contain 5 or 6 atoms.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENT

The present invention is illustrated in further details by the following non-limiting examples.

Materials: Hydrogen peroxide (30% and 50%) was obtained from Fisher Chemicals (Thermo Fisher Scientific, Waltham, Mass.). Sheets of softwood spruce fiber (Temalfa93) were obtained from Tembec Inc., Temiscamingue, QC, Canada. Samples of sawdust were obtained as waste product from softwood milling.

Example 1—Production of Carboxylated NCC from Sawdust

A solution of 30% $H_2O_2$ in water (250 mL) was refluxed at 115° C. 20 g of sawdust were added to the $H_2O_2$ solution liquid and the mixture was stirred vigorously for 8.5 hours. The suspension was initially brown in color, but turned white during the reaction. The white suspension of carboxylated NCC settled after the reaction was stopped. Then, 250 mL of distilled water at room temperature were added to the mixture. The carboxylated NCC was then puffed by repeated centrifugation, discarding the supernatant between steps (see Example 4).

Carboxylated NCC particle dimensions were determined by TEM (FIG. 1) after staining with uranyl acetate. Long dimensions ranged between 150-200 nm, with widths ranging between 5-10 nm.

Figure 2:
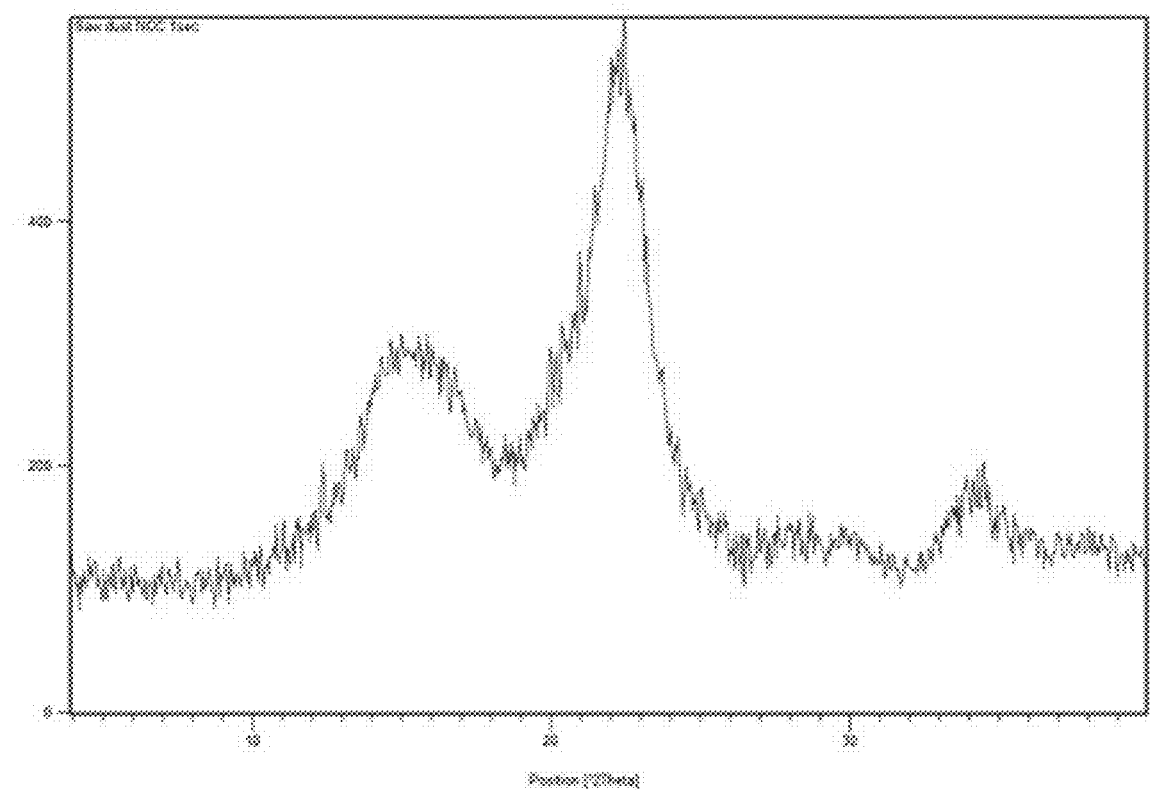
FIG. 2 is the powder X-ray diffraction (XRD) pattern of the carboxylated NCC produced in Example 1.

Wide angle XRD (FIG. 2) revealed that the d-spacing resembles that of crystalline cellulose I.

Figure 3:
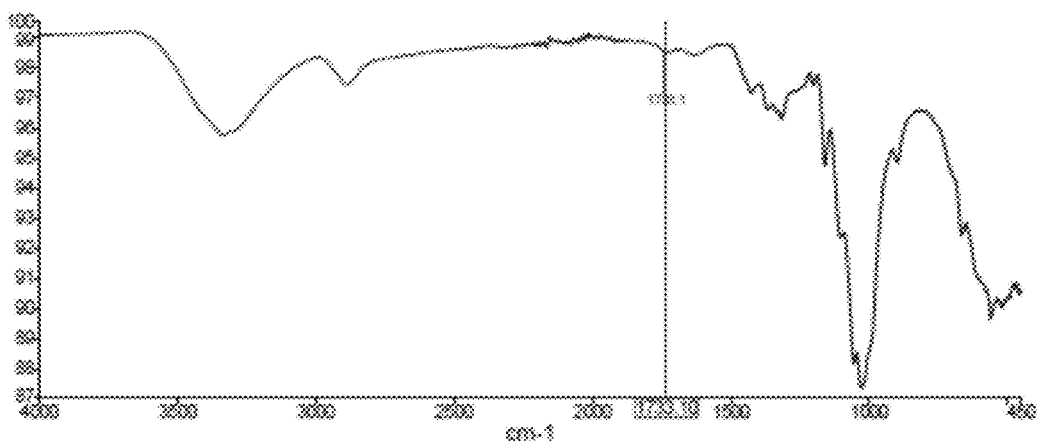
FIG. 3 is the FTIR spectrum of the carboxylated NCC produced in Example 1.

The FTIR spectrum of the produced carboxylated NCC (FIG. 3) exhibits a band associated with the carboxylic acid (C=O) stretching mode at 1732 $cm^{-1}$.

Example 2—Production of NCC Sodium Carboxylate from Temalaf93

A solution of 30% $H_2O_2$ in water (250 mL) was refluxed at 115° C. A softwood spruce fiber (Temalfa93) sheet was cut into 1 cm×5 cm strips. 20 g of these cellulose strips were added to the $H_2O_2$ solution. This mixture was stirred vigorously for 8 hours. This reaction produced a white suspension of NCC that settled when stirring was stopped. Then, 250 mL of distilled water at room temperature were added to the mixture. The carboxylated NCC was then purified by diafiltration and salified as described in Example 5 below.

Figure 4:
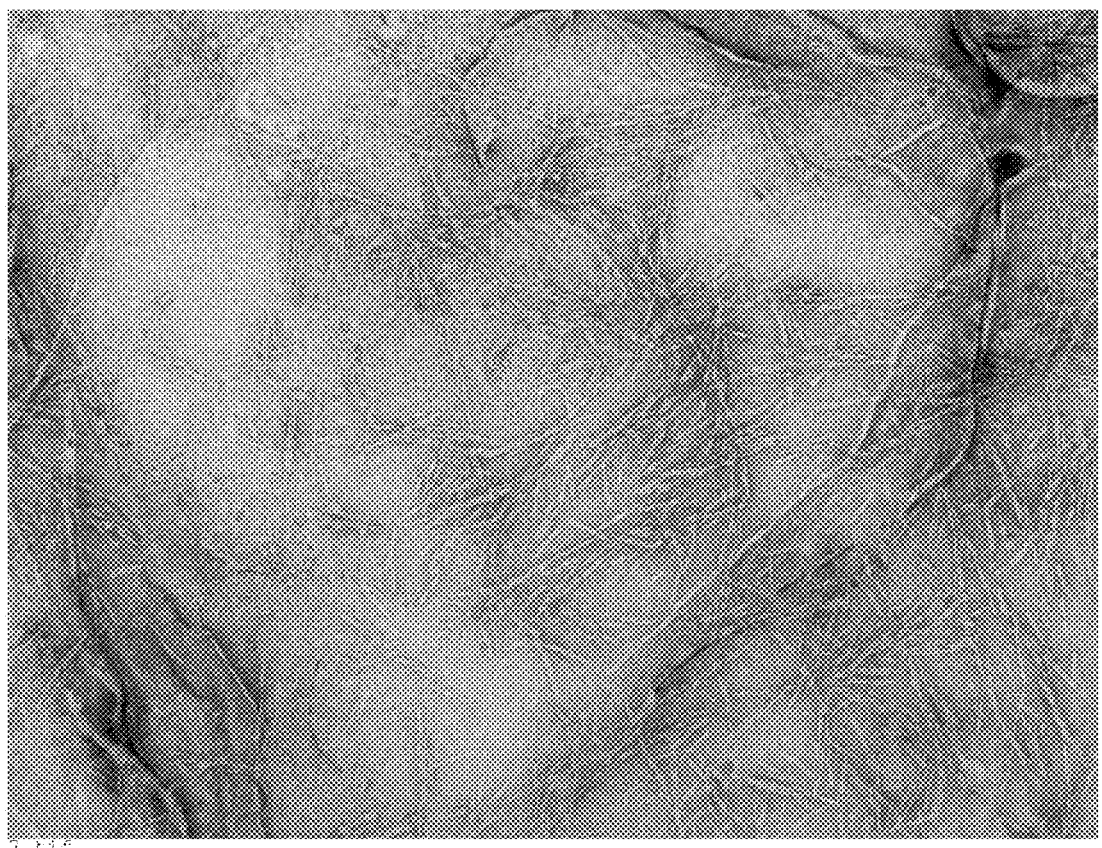
FIG. 4 is the transmission electron micrograph (TEM) of the NCC sodium carboxylate produced in Example 2.

NCC particle dimensions were determined by transmission electron microscopy (TEM) (FIG. 4) after staining with uranyl acetate. Long dimensions ranged between 150-200 nm, with widths ranging between 5-10 nm.

Figure 5:
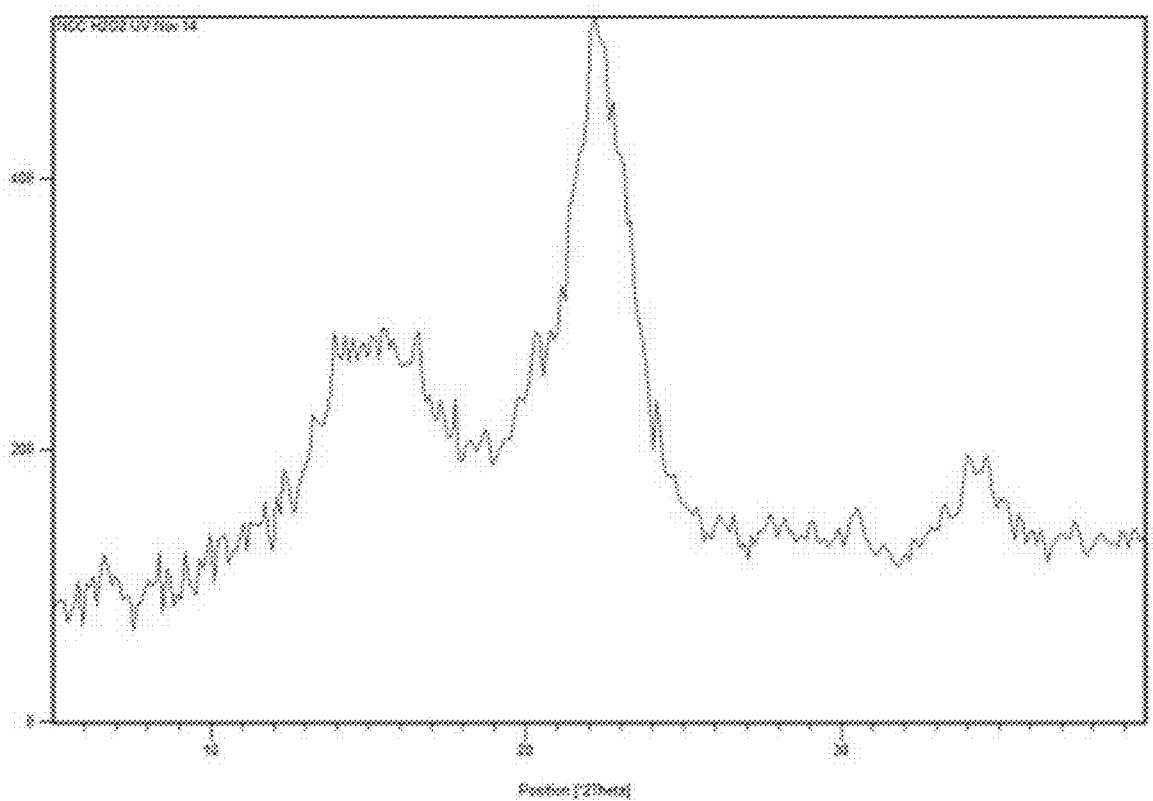
FIG. 5 is the powder XRD pattern of NCC sodium carboxylate produced in Example 2.

Wide angle XRD (FIG. 5) reveals that the d-spacing resembles that of crystalline cellulose I.

Figure 6:
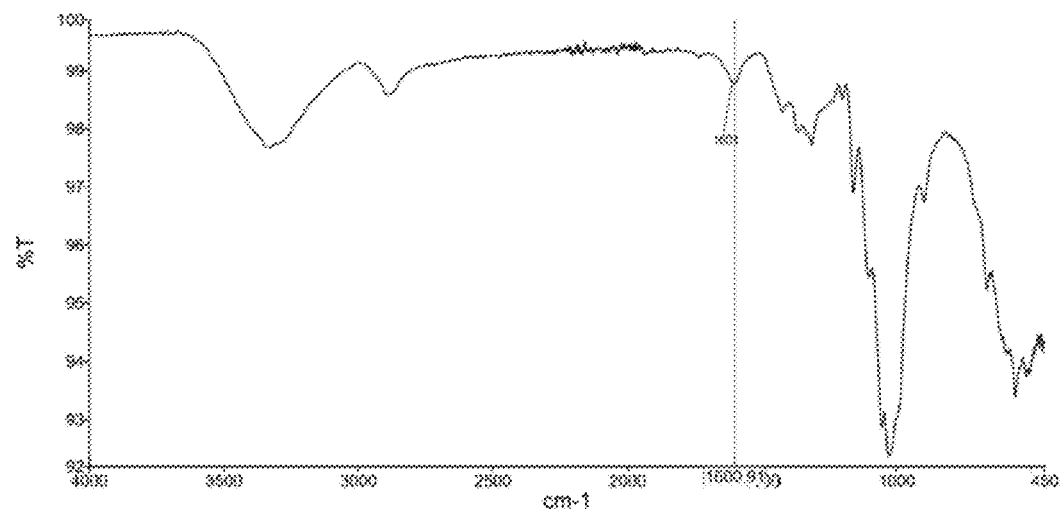
FIG. 6 is the FTIR spectrum of the sodium salt form of NCC sodium carboxylate produced in Example 2.

The FTIR spectrum (FIG. 6) of the produced NCC sodium carboxylate exhibits a band associated with C=O stretching mode at 1600 $cm^{-1}$.

Example 3—Production of NCC Sodium Carboxylate from Temalfa93—with UV Light 10 g Temalfa93, cut into 1 cm×5 cm strips, were added to a room temperature solution of 30% $H_2O_2$ in water (250 mL). A UV light source (unfiltered 220-260 nm wavelength; Oriel model 87530 arc lamp; Oriel 68811 power supply) was then used to irradiate the solution directly from above, under atmospheric air, while stirring the mixture vigorously for 12 hours. The light source was then turned off. The carboxylated NCC was then purified by diafiltration and salified as described in Example 5 below.

Figure 7:
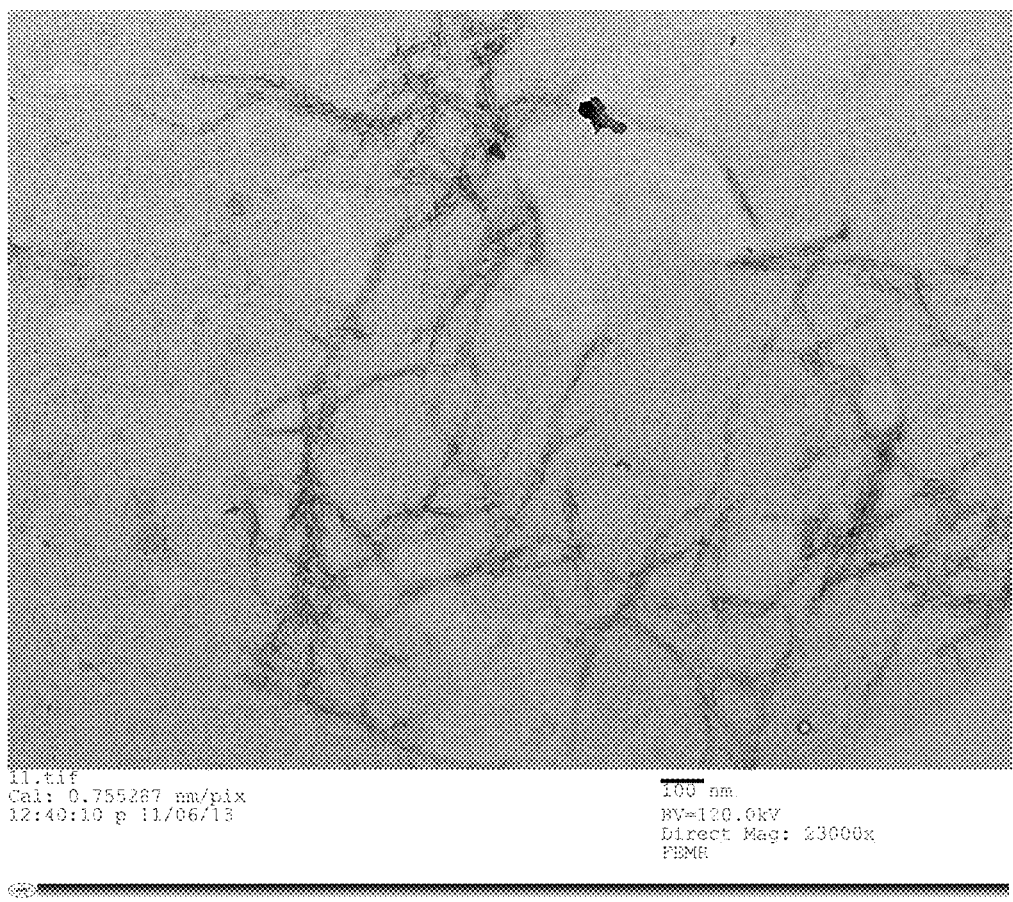
FIG. 7 is the transmission electron micrograph (TEM) of the NCC sodium carboxylate produced in Example 3.

NCC particle dimensions were determined by TEM (FIG. 7) after staining with uranyl acetate. Long dimensions ranged between 150-200 nm, with widths ranging between 5-10 nm.

Figure 8:
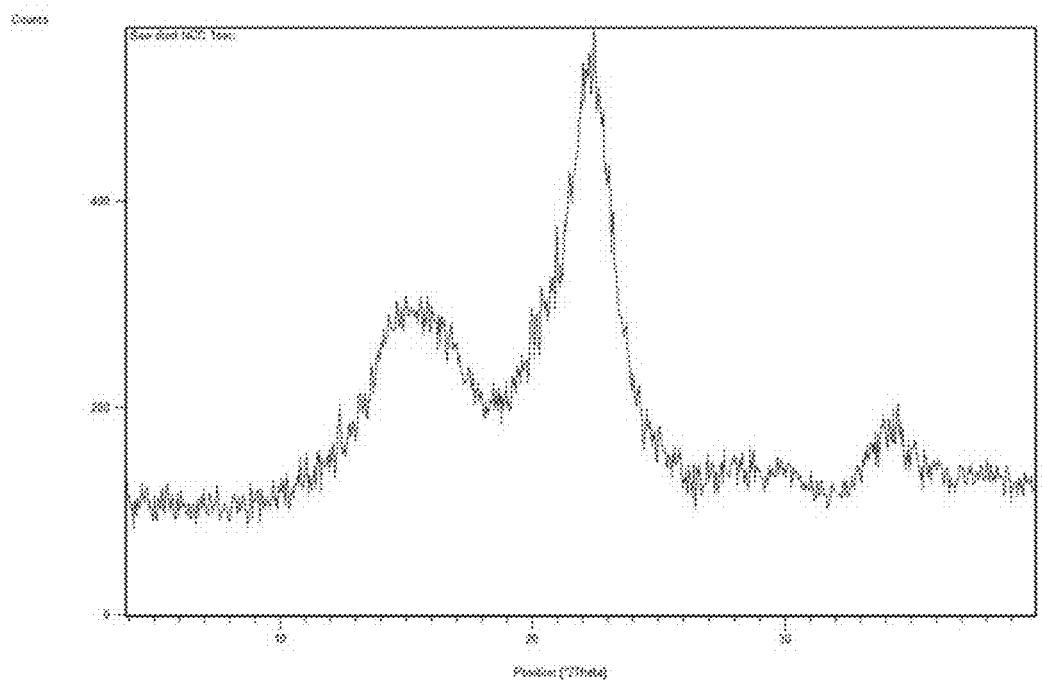
FIG. 8 is the powder XRD pattern of the NCC sodium carboxylate produced in Example 3.

Wide angle XRD (FIG. 8) reveals that the d-spacing resembles that of crystalline cellulose I.

Figure 9:
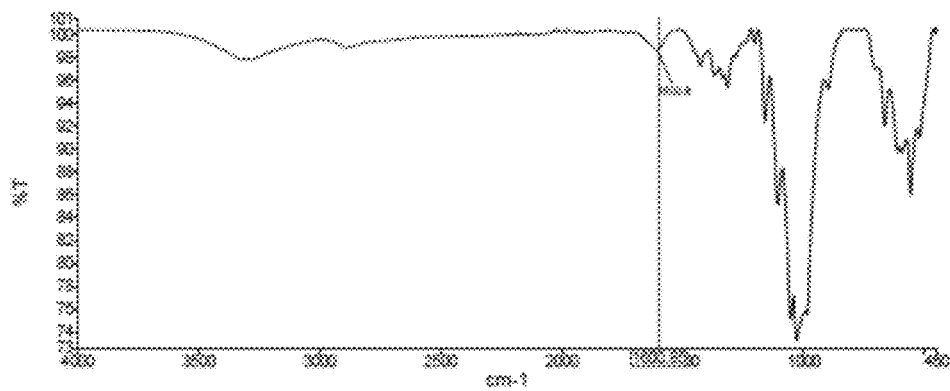
FIG. 9 is the FTIR spectrum of the NCC sodium carboxylate produced in Example 3.

The FTIR spectrum (FIG. 9) of the produced NCC sodium carboxylate exhibits a band associated with C=O stretching mode at 1600 $cm^{-1}$.

Example 4—Purification of Carboxylated NCC by Centrifugation Followed by Salification The reaction suspension was centrifuged at 4000 rpm for 10 minutes. The supernatant was decanted and the pellet was re-suspended in distilled water. Repeated centrifugation/washing cycles were performed until a significant amount of the material remained suspended.

The pH was then brought to 7 using a 1 M NaOH solution, which produced the sodium salt of the carboxylate and gave the nanocrystals a negative charge.

This suspension was then sonicated for 2×5 mins (VCX130 sonicator, Vibracell Sonics and Materials, Inc., Danbury, Conn., USA) at 80% output power to yield a viscous suspension of nanocrystalline cellulose sodium carboxylate, typically 1-2% w/v. Yields were found to be between 20-50%, depending on the cellulose source.

Example 5—Purification of Carboxylated NCC by Diafiltration Followed by Salification The reaction suspension was passed through a diafiltration unit (Masterflex peristaltic pump, model no. 7526-00; Spectrum Labs filter, 100 kDa cutoff). Diafiltration was conducted until the conductivity of the permeate was below 30 µS.

The pH was then brought to 7 with 1 M NaOH to create the sodium salt of the carboxylate and to give the nanocrystals a negative charge.

This suspension was then sonicated for 2×5 mils (VCX130 sonicator, Vibracell Sonics and Materials, Inc., Danbury, Conn., USA) at 80% output power to yield a viscous suspension of nanocrystalline cellulose sodium carboxylate, typically 1-2% w/v. Yields were found to be between 20-50%, depending on cellulose source.

Example 6—Iridescence of Dry and Wet Films

When the sodium salt form of the purified nanocrystalline cellulose (from Example 5) was suspended in water such that the solids content was on the order of 2.5% w/v, the fluid suspension separated into an isotropic and an anisotropic phase. These phases could be distinguished by viewing the suspension through crossed polarizers, or simply by eye. The anisotropic phase was determined to have the properties of a chiral nematic liquid crystal. One of the properties of the liquid crystal phase was that the suspension manifests visible light iridescence, a color-travel phenomenon in which selected wavelengths of light are reflected from the liquid crystal.

When a suspension of the sodium salt of carboxylated nanocrystalline cellulose was cast as a film and allowed to dry in air, the suspension was observed to progress through several changes in color, though the color spectrum, from red to blue. Dry films were transparent to the eye. Light was reflected from the dried film in the region of ultra-violet wavelengths. Scanning electron microscopy revealed that the dried film exhibited a periodic layer (lamellar) structure. The evolution of color as water evaporated from the suspension occurred regardless of whether the suspension was derived solely from the anisotropic phase or from a combination of the anisotropic and isotropic phases. A dried film that was colorless to the eye was observed to express iridescence extending from blue to red (i.e., through the visible color spectral range) when the film was exposed to water. Such changes in color occurred reversibly.

Example 7—Production of Positively Charged NCC (NCC+)

A 1 L suspension of the carboxylate salt of NCC (as prepared above) in water (0.5% w/v, 5 g) was equipped with a stirbar and a Sonics Vibra-cell VCX130 probe sonicator. The suspension was stirred and sonication turned on at 100% output. Immediately following this, 20 mL of a solution of PDDA (Mw<100 kDa) in water (3.5% w/v, 0.7 g) was rapidly added all at once to the carboxylated NCC suspension. Sonication was continued for 40 min to yield a stable viscous suspension.

This product was purified by diafiltration using a 10 kDa MW cut-off filter until conductivity of the permeate was <20 µS. This yielded a stable translucent suspension of positively charged NCC particles (NCC+).

Figure 10:
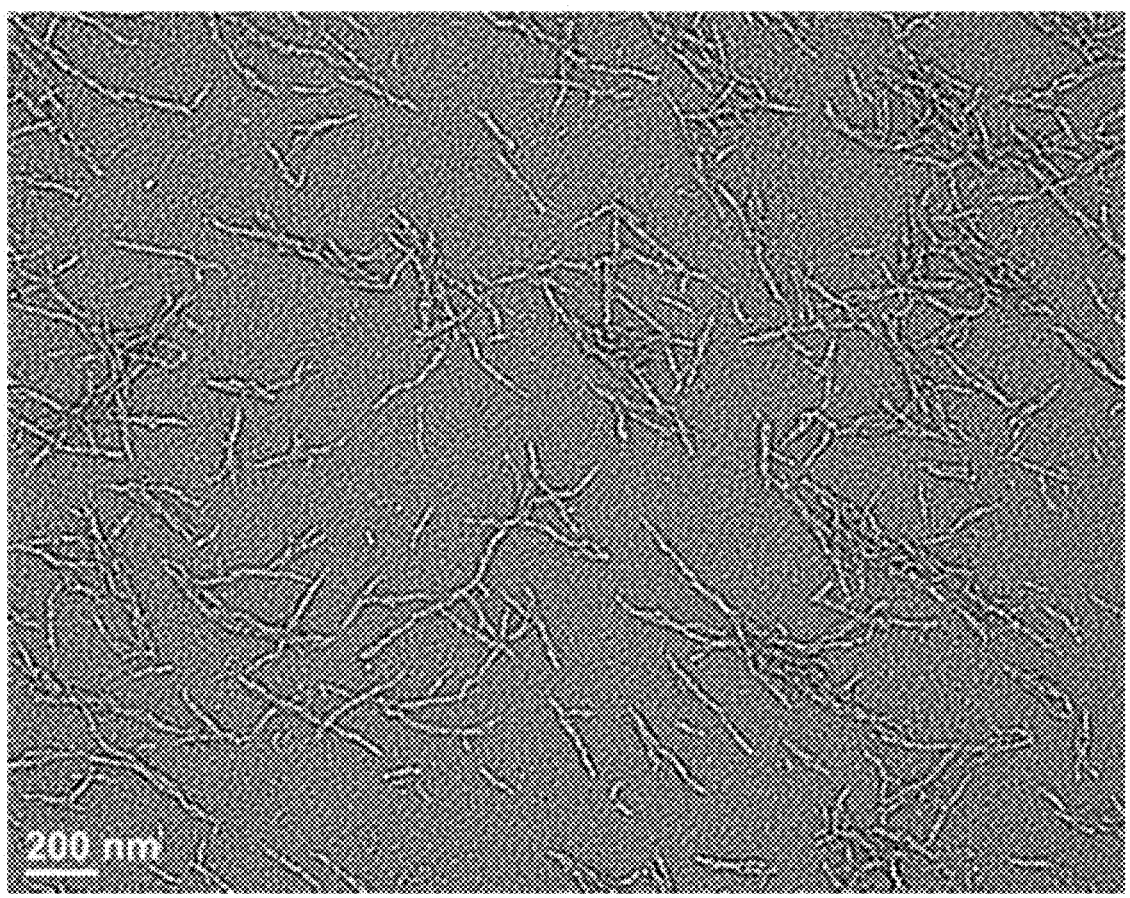
FIG. 10 is the transmission electron micrograph (TEM) of the positively charged NCC produced in Example 7.

Conversion of the negative charge to positive charge on the surface of nanocrystalline cellulose carboxylate salt was followed by monitoring the zeta potential. For example, upon addition of 14% PDDA relative to the carboxylate salt of nanocrystalline cellulose weight, the zeta potential shifted from −42 mV to +59 mV. The resulting product was an aqueous suspension of individually dispersed nanoparticles with an effective diameter of 131 nm, as evidenced by dynamic light scattering (DLS), TEM was also used to show the size of NCC+ with an average length of 198±27 nm (FIG. 10). Importantly, TEM displayed individual nanoparticles prepared in this manner.

Example 8—Spray Drying of NCC Suspensions

Spray drying was performed by using an SD 3.5 Pilot Plant spray dryer on site at Techni Process North America Inc. The inlet temperature was set to 175° C., with an outlet temperature of 68° C. Compressed air pressure was set at 50 psi, resulting in approximately 10 L/h of feed flow to the dryer. Powders were produced by spray drying aqueous suspensions of both carboxylated NCC (4% w/v) and NCC+ (0.75% w/v).

Figure 11:
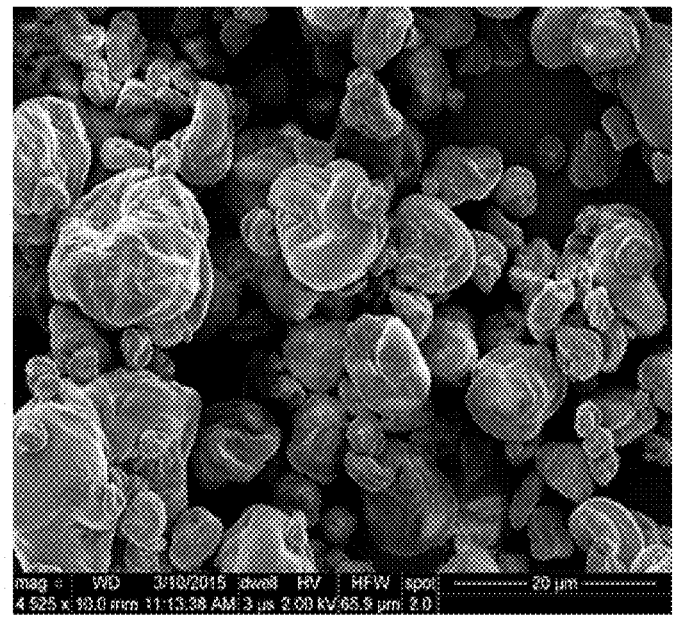
FIG. 11 is the scanning electron micrographs (SEM) of (A) NCC and (B) NCC+ particles spray-dried as prepared in Example 8.
Figure 11:
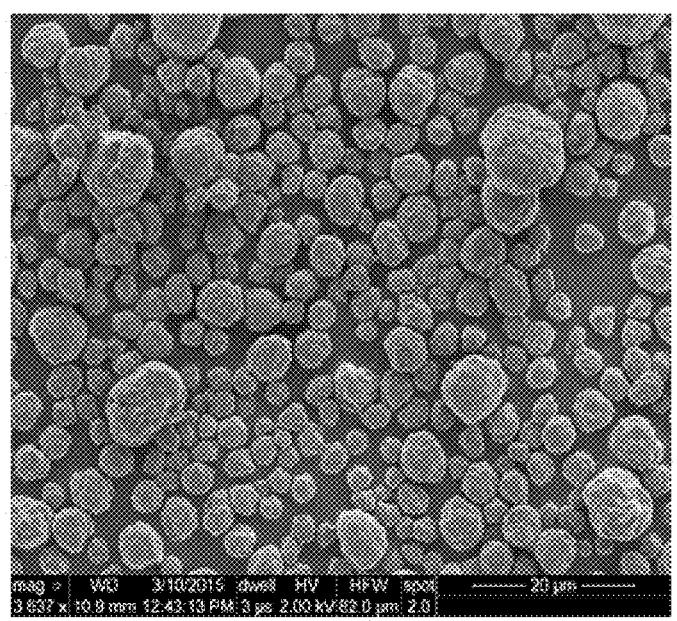

The size and spherical shape of the spray dried powders were imaged by SEM (FIGS. 11A and B). Size ranges were 2.1-8.7 µm for cNCC and 1-3.6 µm for NCC$^+$.

Figure 12:
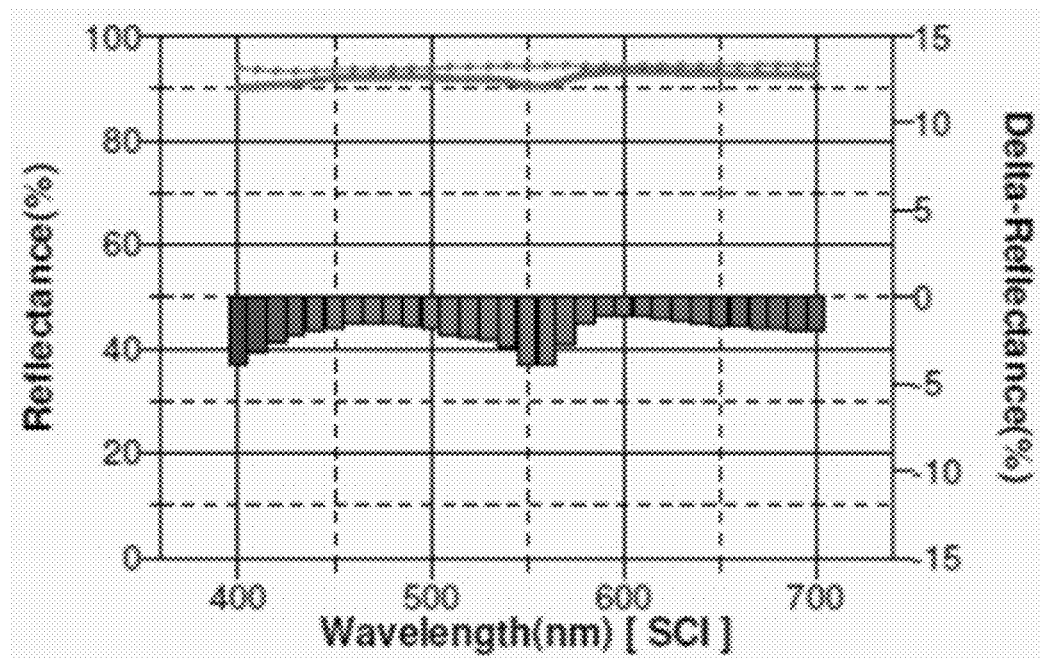
FIG. 12 is the reflectance spectra of (A) NCC and (B) NCC+ particles spray-dried as prepared in Example 8, and that of boron nitride as a comparative (dotted line).
Figure 12:
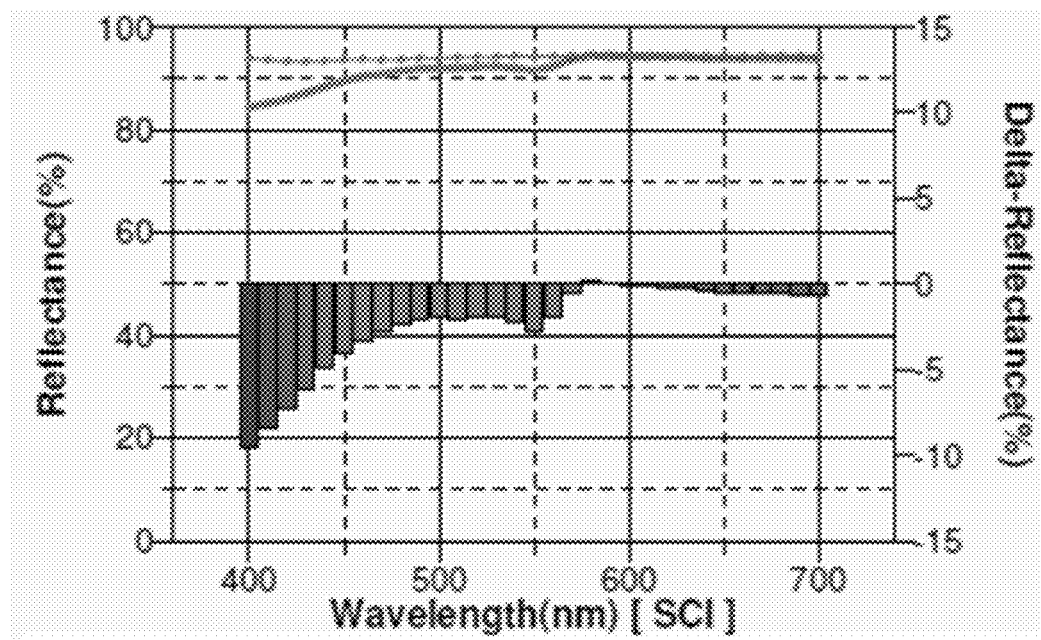

The reflectance spectra of the powders (FIGS. 12A and B) show high reflectance over the visible region. For comparison, the reflectance of boron nitride is also given.

Figure 13:
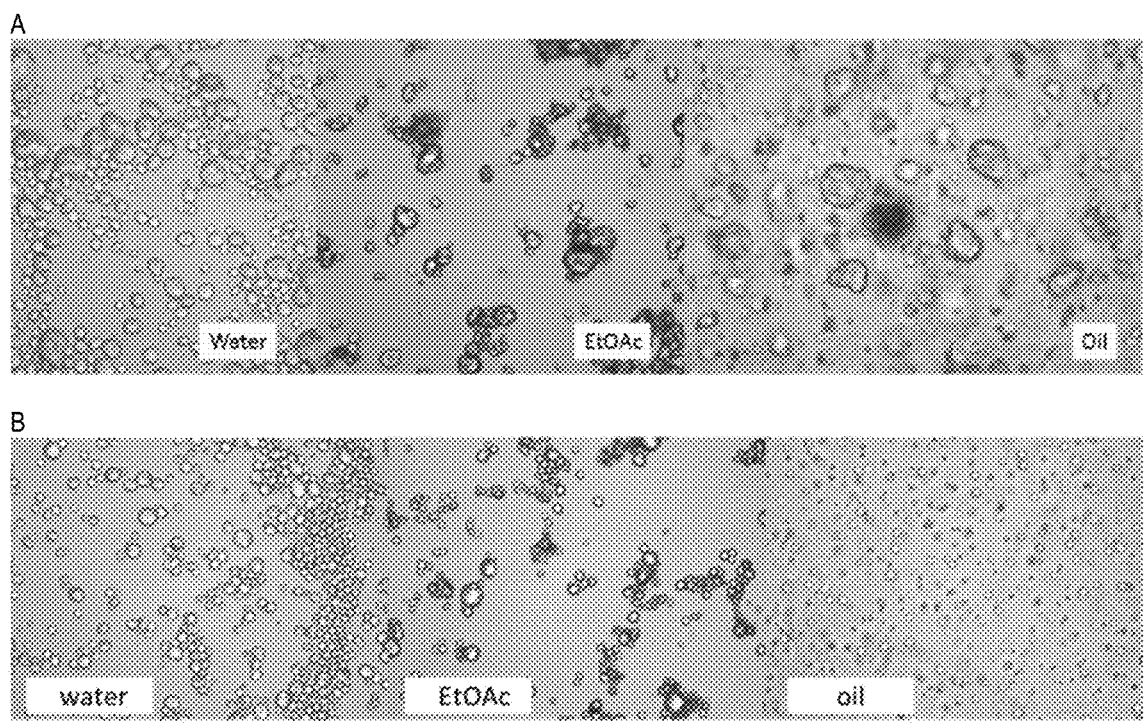
FIG. 13 is the optical micrographs of spray dried particles after 60 days of (A) carboxylated NCC and (B) of NCC+, both being as prepared in Example 8 and both dispersed in water, ethyl acetate or Salacos 222 oil.

Spray dried particles of carboxylated NCC and NCC+ were separately dispersed in water, or ethyl acetate or Salacos 222 oil. In all cases, both categories of particles retain their spherical shape in each of the solvent media (FIGS. 13A and B). The NCC+ version exhibited greater stability against settling in the cosmetic ingredient (Salacos 222). This indicates an advantage of adsorbing the cationic polymer to the surface of the individual NCC particles before spray drying, since the resulting particles are more dispersible and stable in the cosmetic oil medium.

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:
International patent publication WO 00/15720.
International patent publication WO2011/072365.
U.S. Pat. No. 6,238,521.
U.S. Pat. No. 8,541,352.
Babadagli T., Boluk, Y. (2005). Journal of Colloid and Interface Science, 282 162.
Bai, W., Holbery, J., Li, K. (2009). Cellulose 16, 455.
Baranoski G. and Krishnaswamy A., An Introduction to Light Interaction with Human Skin, Revista de Informatica Teorica e Aplicada (RITA) XI, no. 1, 2004, 33-60.
Beck-Candanedo, S., Roman, M., Gray, D. G. (2005). Biomacromolecules, 6, 1048.
Dong, X. M., Revol, J.-F., Gray. D. G. (1998). Cellulose, 5, 19
Dufresne, A. (2010). Molecules, 15, 4111.
Elazzouzi-Hafraoui, S., Nishlyama, Y., Putaux, J. L., Heux, L., Dubreuil, F., Rochas, C. (2008). Biomacromolecules, 9, 57-65.
Filpponen, I., Argyropoulos, D. (2010). Biomacromolecules, 11, 1060.
Habibi, Y., Lucia, L. A., Rojas, O. J. (2010). Chemical Reviews, 110, 3479.
Hasani M., Cranston E., Westman G. and Gray D., Soft Matter, 2008, 4, 2238-2244.
Heath, L., Thielemans, W. (2010). Green Chemistry, 12, 1448.
Holt, B., Sloyanov, S., Pelan, E., Paunov, V. (2010). J. Mater. Chem., 20, 10058.
Iwamoto, S., Kai, W. H., Isogai, A., Iwata, T. (2009). Biomacromolecules, 10, 2571.
Jiang, F., Esker, A. R., Roman, M. (2010). Langmuir, 26, 17919.
Leung, C., Luong, J., Hrapovic, S., Lam, E., Liu, Y., Male, K., Mahmoud, K., Rho, D., (2011) International Patent Publication WO 2011/072365 A1 published Jun. 23, 2011.
Montanan, S., Roumani, M., Heux, L., Vignon, M. (2005). Macromolecules, 38, 1665.
Nickerson, R., Hable, J. (1947). Industrial & Engineering Chemistry, 39, 1507.
Nishikata et al., Cosmetics and Toiletries, 112, 39-55, 1997.
Nishino, T., Matsuda, I., Hirao, K. (2004). Macromolecules, 37, 7683.
Oksnnan, K., Bodesman, D., Syre, P. (2008) United States Patent Publication 2008/01087721 A1 published May 8, 2008.
Peng, B. Dhar, N., Liu, L., Tam, K. (2010). The Canadian Journal of Chemical Engineering, 9999, 1.
Revd, J.-F., Bradford, H., Marchessault, R. H., Gray, D. G. (1992). Int. J. Biol Macromol. 14, 1, 70.
Sadeghifar, H., Filpponen, I., Clarke, S. P., Brougham, D. F., Argyropoulos, D. S. (2011). Journal of Materials Science, 46, 7344.
Suchy, M., Argyropoulos, D. S. (2002). TAPPI Journal, 1,1.
Wong, A., Chiu, C. International Patent Publication WO 94/05851 published Mar. 17, 1994.
Zuluaga, R., Putaux, J. L., Restrepo, A., Mondragon, I., Ganan, P. (2007). Cellulose, 14, 585.

The invention claimed is:
1. A method for producing functionalized nanocrystalline cellulose in the form of nanocrystals in one step, wherein the nanocrystals are between about 2 nm to about 20 nm in width and between about 80 nm and about 250 nm in length, the method comprising the steps of:
  (a) providing cellulose,
  (b) mixing said cellulose with a peroxide, thereby producing a reaction mixture, and
  (c) heating and/or (c') exposing to UV radiation the reaction mixture containing the cellulose and the peroxide until hydrolysis and oxidation by the peroxide of the cellulose into carboxylated nanocrystalline cellulose, steps (c) and/or (c') thereby producing carboxylated nanocrystalline cellulose that is free of surface sulfate groups as said functionalized nanocrystalline cellulose;

wherein the carboxylated nanocrystalline cellulose is produced at steps (c) and/or (c') in the absence of mineral acids or inorganic persulfates; and wherein the method does not comprise TEMPO oxidation.

2. The method of claim 1, wherein the peroxide is hydrogen peroxide, an organic peroxide, or a mixture thereof.

3. The method of claim 1, wherein the peroxide is present in the reaction mixture at a concentration between about 10 to about 40%.

4. The method of claim 1, wherein the reaction mixture is heated in step (c) at a temperature up to and including reflux.

5. The method of claim 1, wherein the reaction mixture is exposed in step (c') to UV radiation in the range from about 200 to about 350 nm.

6. The method of claim 5, wherein the reaction mixture is exposed in step (c') to UV radiation in the range from about 260 to about 280 nm.

7. The method of claim 1, wherein the reaction mixture is at a temperature in the range of 15-30° C. during step (c').

8. The method of claim 1, further comprising the step (d) of salifying the functionalized nanocrystalline cellulose, thereby producing a nanocrystalline cellulose carboxylate salt as a further functionalized nanocrystalline cellulose.

9. The method of claim 8, further comprising the step (e) of positively charging the surface of the nanocrystalline carboxylate salt cellulose by:

(e') providing an aqueous suspension of the nanocrystalline cellulose carboxylate salt, (e") mixing said suspension with a water soluble cationic polyelectrolyte to form a reaction mixture, and (e''') sonicating the reaction mixture, thereby producing an aqueous suspension of a nanocrystalline cellulose carboxylate salt having a positive surface charge as a further functionalized nanocrystalline cellulose.

10. The method of claim 9, further comprising step (f) of isolating the functionalized nanocrystalline cellulose and wherein said isolation is carried out by centrifugation or diafiltration.

11. The method of claim 10, further comprising step (h) of recycling unreacted peroxide.

12. The method of claim 1, further comprising step (g) of spray-drying the functionalized nanocrystalline cellulose.

13. The method of claim 1, wherein the peroxide is aqueous hydrogen peroxide.

14. The method of claim 1, wherein the reaction mixture is heated in step (c) to reflux.

15. The method of claim 1, wherein step (c) is carried out and step (c') is not carried out.

16. The method of claim 1, wherein step (c') is carried out and step (c) is not carried out.

17. The method of claim 1, wherein steps (c) and (c') are carried out consecutively.

18. The method of claim 1, wherein at least part of steps (c) and (c') are carried out concurrently.

19. The method of claim 1, wherein all of the steps (c) and (c') are carried out concurrently.

* * * * *